United States Patent
Ohmiya

(10) Patent No.: US 9,546,951 B2
(45) Date of Patent: Jan. 17, 2017

(54) REDUCING POWER ANALYSIS METHOD AND REDUCING POWER ANALYSIS REAGENT

(71) Applicant: ARKRAY, Inc., Kyoto (JP)

(72) Inventor: Kazuhiro Ohmiya, Kyoto (JP)

(73) Assignee: ARKRAY, Inc., Kyoto (JP)

(*) Notice: Subject to any disclaimer, the term of this patent is extended or adjusted under 35 U.S.C. 154(b) by 0 days.

(21) Appl. No.: 14/665,440

(22) Filed: Mar. 23, 2015

(65) Prior Publication Data
US 2015/0276585 A1    Oct. 1, 2015

(30) Foreign Application Priority Data

Mar. 26, 2014  (JP) .................. 2014-063735
Mar. 18, 2015  (JP) .................. 2015-054883

(51) Int. Cl.
G01N 21/31   (2006.01)
G01N 33/50   (2006.01)
G01N 33/52   (2006.01)
G01N 21/78   (2006.01)

(52) U.S. Cl.
CPC .............. *G01N 21/31* (2013.01); *G01N 21/78* (2013.01); *G01N 33/52* (2013.01); *G01N 2021/3196* (2013.01)

(58) Field of Classification Search
CPC ........................... G01N 21/31; G01N 21/3196
See application file for complete search history.

(56) References Cited

U.S. PATENT DOCUMENTS

| | | | | |
|---|---|---|---|---|
| 5,053,429 A | * | 10/1991 | Hirsch | A61K 31/195 514/562 |
| 2003/0235571 A1 | * | 12/2003 | Gojon-Romanillos | A61K 31/095 424/94.1 |
| 2007/0054347 A1 | * | 3/2007 | Rosendahl | A61B 5/14542 435/25 |
| 2011/0152371 A1 | * | 6/2011 | Rupasinghe | A23D 7/0053 514/560 |
| 2013/0252261 A1 | | 9/2013 | Opperman et al. | |

FOREIGN PATENT DOCUMENTS

| | | |
|---|---|---|
| EP | 2362227 A1 | 8/2011 |
| JP | 2009-257909 A | 11/2009 |

OTHER PUBLICATIONS

Extended European Search Report issued in corresponding European Patent Application No. 15161034.2 dated Jul. 2, 2015.

\* cited by examiner

*Primary Examiner* — Paul Hyun
(74) *Attorney, Agent, or Firm* — Morgan, Lewis & Bockius LLP

(57) ABSTRACT

A reducing power analysis method for minimizing peak wavelength shift in a sample, comprising a reduction step of reducing a dye reagent containing a ferric compound and a cyanide at pH conditions of 2.4 or lower in the presence of a sample; and an optical measurement step of optically measuring a peak wavelength of a reduced form of the dye reagent obtained in the reduction step.

12 Claims, 3 Drawing Sheets

FIG. 3A  Sulfuric acid
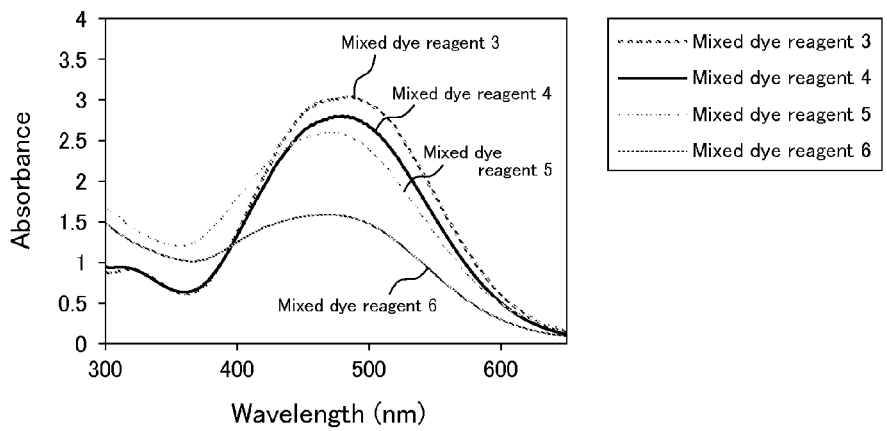
FIG. 3B  Propionic acid
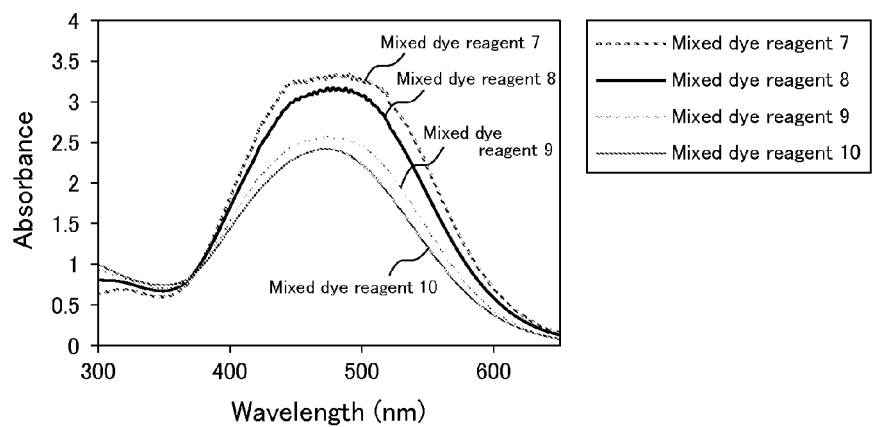
FIG. 3C  p-toluenesulfonic acid
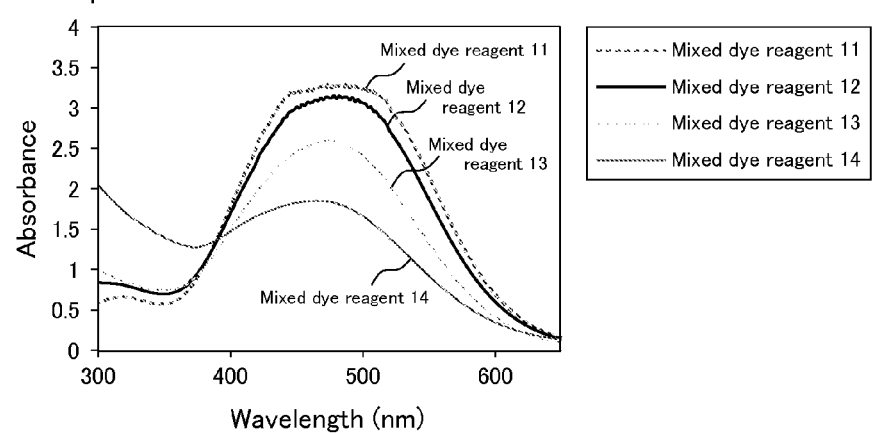

REDUCING POWER ANALYSIS METHOD AND REDUCING POWER ANALYSIS REAGENT

BACKGROUND OF THE INVENTION

1. Field of the Invention

The present invention relates to a reducing power analysis method and a reducing power analysis reagent.

2. Description of Related Art

Under oxidative stress conditions, proteins, lipids, DNAs, and the like are damaged by peroxides and free radicals generated in vivo. It is known that accumulation of such damage may lead to cardiovascular diseases, nervous system diseases, and the like, for example. On the other hand, it also is known that such peroxides and free radicals can be rendered harmless with antioxidants, which have reducing power, present in vivo. In view of this, there have been attempts to prevent the above-described diseases or to understand the pathological conditions of these diseases by analyzing the reducing power of antioxidants, which is one of the indicators of resistance to oxidative stress.

A dye reagent colored blood red by a reaction between trivalent iron ions and a cyanide fades when reduced. Thus, the reducing power of a sample has conventionally been analyzed by bringing a dye reagent into contact with a sample to reduce the dye reagent by the sample, and then, optically measuring the resulting degree of the fading of the dye reagent (Patent Document 1).

CITATION LIST

Patent Document(s)

Patent Document 1: JP 2009-257909 A

BRIEF SUMMARY OF THE INVENTION

Problem to be Solved by the Invention

The inventors of the present invention discovered that, when the reducing power of a sample is analyzed by a reducing power analysis method utilizing the dye reagent containing trivalent iron ions and a cyanide, there arises a problem that the peak wavelength of an optical signal of a reaction system containing the dye reagent and the sample may shift. If the peak wavelength shift of the optical signal occurs, the result is that the actual optical signal of a sample is different from the apparent optical signal of the sample obtained through measurement. Thus, the reducing power calculated on the basis of the optical signal also is incorrect, resulting in insufficient reliability on the quantitative analysis result.

Therefore, with the foregoing in mind, it is an objective of the present invention to provide a reducing power analysis method that can analyze the reducing power of a sample while preventing a shift in the peak wavelength of an optical signal.

Means for Solving Problem

In order to solve the above-described problem, the present invention provides a reducing power analysis method comprising: a reduction step of reducing a dye reagent containing a ferric compound and a cyanide at pH conditions of 2.4 or lower in the presence of a sample; and an optical measurement step of optically measuring a peak wavelength of a reduced form of the dye reagent obtained in the reduction step.

The present invention also provides a reducing power analysis reagent for use in the reducing power analysis method according to the present invention, containing: a dye reagent containing a ferric compound and a cyanide; and a pH adjuster, wherein the pH adjuster is a strongly acidic reagent.

Effects of the Invention

The inventors of the present invention discovered as a result of a diligent study that, in the analysis of the reducing power of a sample, the shift of the peak wavelength of an optical signal in a reaction system containing the dye reagent and the sample is caused by albumin and methionine contained in the sample. The inventors of the present invention further discovered that the shift of the peak wavelength of an optical signal in the reaction system can be prevented by carrying out the reduction step at pH conditions of 2.4 or lower, although the mechanism thereof is unknown. Thus, the inventors of the present invention achieved the present invention. As a result, according to the present invention, the analysis of the reducing power of a sample can be carried out without being influenced by the components of the sample, so that a shift in the peak wavelength of an optical signal in the reaction system can be prevented. Therefore, the present invention makes it possible to reduce an error caused when the reducing power is analyzed on the basis of an optical signal, with the result that the reducing power of a sample can be analyzed with higher reliability. Accordingly, the present invention is very useful in clinical tests and the like of various samples derived from living organisms and the like, for example.

BRIEF DESCRIPTION OF THE DRAWINGS

FIGS. 3A to 3C are graphs each showing the results of absorbance measurements in Example 2.

DETAILED DESCRIPTION OF THE INVENTION

<Reducing Power Analysis Method>

Figure 1:
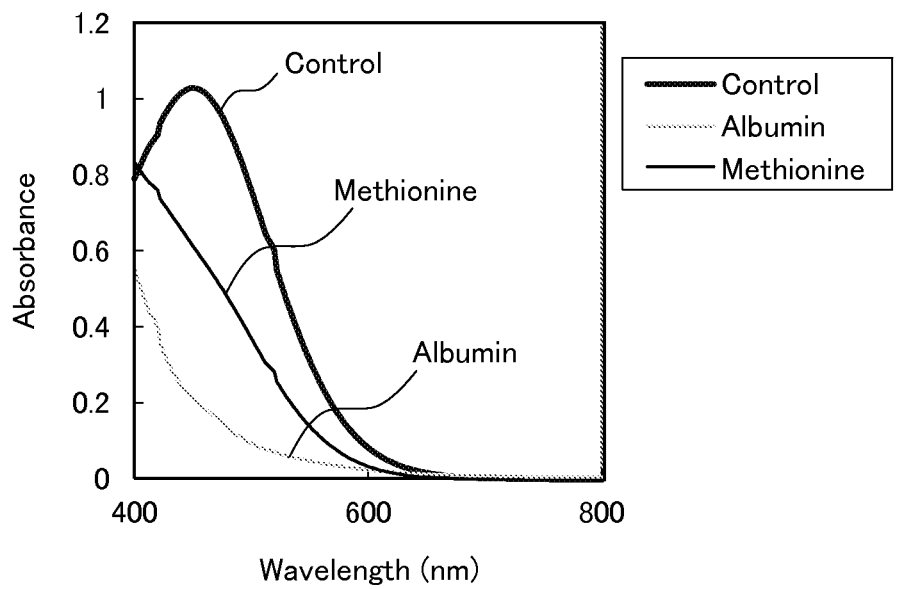
FIG. 1 is a graph showing the results of absorbance measurements in Example 1.

As described above, the reducing power analysis method according to the present invention includes: a reduction step of reducing a dye reagent containing a ferric compound and a cyanide at pH conditions of 2.4 or lower in the presence of a sample; and an optical measurement step of optically measuring a peak wavelength of a reduced form of the dye reagent obtained in the reduction step. The analysis method of the present invention is characterized in that the reduction step is carried out at pH conditions of 2.4 or lower, and other steps and conditions are not particularly limited. As described above, the analysis method of the present invention prevents the shift of the peak wavelength of an optical signal in the reaction system. Thus, the analysis method of the present invention also can be referred to as a method for preventing a peak wavelength shift. In the present invention, the reduction of the dye reagent in the reduction step is achieved by the reducing power of the sample. In the optical measurement step, "the reduced form of the dye reagent obtained in the reduction step" refers to the reduced dye reagent.

The analysis method of the present invention may be, for example, a qualitative analysis for analyzing whether or not the sample has reducing power or a quantitative analysis for analyzing the level of the reducing power of the sample.

In the present invention, the reduction step is carried out at pH conditions of 2.4 or lower. In other words, the analysis method of the present invention is such that, for example, in the reduction step, the pH of the reaction system containing the sample and the dye reagent is at 2.4 or lower. Preferably, the pH of the reaction system is adjusted to 2.4 or lower when the dye reagent and the sample are brought into contact with each other or after they have brought into contact with each other, for example. The reaction system preferably is, for example, a liquid system, which also can be referred to as a reaction solution or a reduction solution containing the sample and the dye reagent.

In the analysis method of the present invention, the sample is not particularly limited. Because the peak wavelength shift occurs under the influence of albumin and methionine as described above, the present invention is applicable to a sample containing at least one of albumin and methionine, for example. The sample may be a biological sample, for example. Specific examples of the biological sample include blood, saliva, urine, tear, and sweat. The blood may be, for example, erythrocytes, whole blood, serum, plasma, or the like. Among them, whole blood is preferable.

The sample preferably is in the form of a liquid (liquid sample) from the viewpoint of ease of handling, for example. The sample may be used as a liquid sample as is without dilution, or as a diluted solution obtained by suspending, dispersing, or dissolving the sample in a solvent, for example. When the sample is a solid, a diluted solution obtained by suspending, dispersing, or dissolving the sample in a solvent may be used as a liquid sample, for example. The solvent is not particularly limited, and may be, for example, water, a buffer solution, or the like. The buffer solution is not particularly limited, and examples thereof include a Tris buffer, an acetate buffer, a borate buffer, a citrate buffer, a veronal buffer, and various Good's buffers. The concentration of the buffer solution is not particularly limited, and may be 10 to 100 mmol/L, for example.

In the analysis method of the present invention, the dye reagent is not particularly limited, and may be a cyanide-iron complex containing the ferric compound and the cyanide, for example. The cyanide-iron complex is not particularly limited, and examples thereof include a thiocyanate-iron complex ($[Fe(NCS)(H_2O)_5]^{2+}$) and a ferricyanide-iron complex ($[Fe(CN)_6]^{3-}$).

In the analysis method of the present invention, the ferric compound is not particularly limited, and examples thereof include iron(III) chloride and iron(III) sulfate. In the analysis method of the present invention, one kind of ferric compound may be used, or two or more kinds of ferric compounds may be used in combination, for example.

In the analysis method of the present invention, the cyanide is not particularly limited, and may be, for example, a thiocyanate, a ferricyanide, or the like. The thiocyanate is not particularly limited, and examples thereof include potassium thiocyanate, sodium thiocyanate, and ammonium thiocyanate. In the analysis method of the present invention, one kind of cyanide may be used, or two or more kinds of cyanides may be used in combination, for example.

In the reduction step, the order of adding the dye reagent and the sample is not particularly limited, for example. For example, as the dye reagent, a cyanide-iron complex containing the ferric compound and the cyanide (hereinafter also referred to as a "mixed dye reagent") may be provided in advance, and the cyanide-iron complex then may be mixed with the sample. Alternatively, the ferric compound, the cyanide, and the sample may be mixed together, thereby achieving the state where a mixed dye reagent containing the ferric compound and the cyanide is mixed with the sample. In the reduction step, the above-described solvent further may be added, for example.

In the former case, for example, the ferric compound and the cyanide may respectively be added to separate solvents, and the mixture of the resultant solutions may be used as the mixed dye reagent. Alternatively, the ferric compound and the cyanide may be added to a solvent, and the resultant solution may be used as the mixed dye reagent. Examples of the solvent include those described above as examples of the solvent to be mixed with the sample. In the latter case, for example, the ferric compound, the cyanide, and the sample may be added to and mixed with the solvent.

In the reduction step, the composition ratio of the reaction system containing the sample and the dye reagent is not particularly limited. The proportion (v/v %) of the sample in the reaction system is not particularly limited, and is, for example, 50% to 99%, preferably 80% to 99%, and more preferably 90% to 99%. It is preferable that, in the reaction system, the proportion of the sample in an undiluted state is in the above-described range.

In the reaction system, the concentration of the dye reagent is not particularly limited. The concentration of the dye reagent in the reaction system can be represented, for example, using the concentrations of the cyanide and the ferric compound as the components of the dye reagent. In the reaction system, the concentration (C) of the cyanide contained in the dye reagent is, for example, 0.006 to 0.09 mol/L, preferably 0.018 to 0.09 mol/L, and more preferably 0.05 to 0.075 mol/L, and the concentration (F) of the ferric compound contained in the dye reagent is, for example, 0.0001 to 0.002 mol/L, preferably 0.00015 to 0.001 mol/L, and more preferably 0.0002 to 0.0003 mol/L. The concentration of the dye reagent may be, for example, the concentration of one kind of dye reagent, or the total concentration of the concentrations of two or more kinds of dye reagents (the same applies hereinafter).

In the reaction system, the mixing ratio between the ferric compound contained in the dye reagent and the sample is not particularly limited. With respect to 1 mL of the sample, the amount of the ferric compound is, for example, 0.0016 to 0.032 mmol, preferably 0.0024 to 0.016 mmol, and more preferably 0.0032 to 0.0048 mmol.

In the reaction system, the mixing ratio between the cyanide contained in the dye reagent and the sample is not particularly limited. With respect to 1 mL of the sample, the amount of the cyanide is, for example, 0.096 to 1.44 mmol, preferably 0.288 to 1.44 mmol, and more preferably 0.8 to 1.12 mmol.

In the reaction system, the proportion of the ferric compound contained in the dye reagent may be in the proportion of one kind of ferric compound, or may be in the total proportion of two or more kinds of ferric compounds (the same applies hereinafter). In the reaction system, the proportion of the cyanide contained in the dye reagent may be in the proportion of one kind of cyanide, or in the total proportion of the proportions of two or more kinds of cyanides (the same applies hereinafter).

In the reaction system, the ratio (the molar ratio F:C) between the ferric compound (F) and the cyanide (C) is not particularly limited, and is, for example, 1:24 to 1:357, preferably 1:72 to 1:357, and more preferably 1:200 to 1:300.

In the reduction step, the pH of the reaction system containing the dye reagent and the sample is, for example, 2.4 or lower, preferably 2.3 or lower. The pH of the reaction system may be adjusted by, for example: mixing the dye reagent with the sample; or mixing the dye reagent with the sample and then adding a pH adjuster to the mixture. In the former case, for example, the pH of the dye reagent may be adjusted in advance so that the above pH conditions are satisfied when the dye reagent is mixed with the sample. In the present invention, the pH of the reaction system during the reduction step is 2.4 or lower, as described above.

The pH adjuster is not particularly limited, and a strongly acidic reagent can be used, for example. The strongly acidic reagent preferably is the one that substantially does not serve as an oxidizing agent or a reducing agent, for example. Specific examples of the strongly acidic reagent include sulfuric acid, propionic acid, and p-toluenesulfonic acid. One strongly acidic reagent may be used, or two or more types of strongly acidic reagents may be used in combination, for example.

In the reaction system, the concentration of the pH adjuster is not particularly limited, and is, for example, 0.001 to 1 mol/L, preferably 0.001 to 0.1 mol/L, and more preferably 0.002 to 0.01 mol/L. In the reaction system, the concentration of the pH adjuster may represent, for example, the concentration of one pH adjuster, or may reflect the total concentration of the concentrations of two or more types of pH adjusters (the same applies hereinafter).

In the reaction system, the mixing ratio between the pH adjuster and the sample is not particularly limited. With respect to 1 mL of the sample, the amount of the pH adjuster is, for example, 0.016 to 16 mol, preferably 0.016 to 1.6 mol, and more preferably 0.032 to 0.16 mol.

In the reduction step, the treatment conditions after the dye reagent is mixed with the sample and before the reaction system is subjected to the subsequent optical measurement step is not particularly limited. In the reduction step, the reaction system may be incubated at a predetermined temperature, or may not be incubated, for example. The incubation temperature is, for example, 1° C. to 40° C., preferably 25° C. to 30° C. The incubation time is not particularly limited.

In the optical measurement step, an optical signal to be measured is, as described above, an optical signal of the reduced form of the dye reagent obtained in the reduction step. For example, an optical signal to be measured with regard to the reaction system containing the sample and the dye reagent obtained in the reduction step corresponds to an optical signal of the reduced form of the dye reagent. The optical signal is not particularly limited, and may be, for example, an absorbance, a reflectance, a transmittance, or the like.

In the optical measurement step, the wavelength range in which the peak wavelength is measured optically is not particularly limited, and can be determined as appropriate depending on the kind of the dye reagent. When the dye reagent contains iron(III) chloride and potassium thiocyanate, the peak wavelength is, for example, in the range from 360 to 630 nm, preferably in the range from 400 to 550 nm, and more preferably in the range from 450 to 550 nm. In the optical measurement step, the optical measurement may be carried out with respect to one point in the range, with respect to part of the range, or over the whole range.

In the optical measurement step, for example, the optical signal obtained by optically measuring the peak wavelength may be determined as the reducing power of the sample, or the reducing power of the sample may be calculated indirectly on the basis of the optical signal obtained by optically measuring the peak wavelength. The method for indirectly calculating the reducing power of the sample is not particularly limited, and examples thereof include calculating the reducing power on the basis of the correlation between the optical signal and the reducing power, for example.

The analysis method of the present invention will be described below with reference to an illustrative embodiment. It is to be noted, however, that the present invention is not limited to the following illustrative embodiment. In the embodiment, the components of the dye reagent are iron(III) chloride as the ferric compound and potassium thiocyanate as the cyanide; the sample is blood, which is a biological sample; the pH adjuster is sulfuric acid, which is the strongly acidic reagent; the reduction solution (reaction solution) having a pH of 2.4 or lower is prepared in the reduction step; and the reducing power is analyzed by optically measuring the peak wavelength of the reduction solution having a pH of 2.4 or lower.

First, blood is provided as the biological sample. Then, iron(III) chloride and potassium thiocyanate are mixed with the blood. Sulfuric acid further is added, whereby the pH of the resultant reduction solution is adjusted to 2.4 or lower.

The amount of the iron(III) chloride to be mixed with the blood is not particularly limited, and is, for example, 0.0016 to 0.032 mmol, preferably 0.0024 to 0.016 mmol, and more preferably 0.0032 to 0.0048 mmol, with respect to 1 mL of the blood. The amount of the potassium thiocyanate to be mixed with the blood is not particularly limited, and is, for example, 0.096 to 1.44 mmol, preferably 0.288 to 1.44 mmol, and more preferably 0.8 to 1.12 mmol, with respect to 1 mL of the blood. The amount of the sulfuric acid to be added is not particularly limited, and is, for example, 0.016 to 16 mol, preferably 0.016 to 1.6 mol, and more preferably 0.032 to 0.16 mol, with respect to 1 mL of the blood. In the reduction solution to which the sulfuric acid has been added, the concentration of the sulfuric acid is not particularly limited, and is, for example, 0.001 to 1 mol/L, preferably 0.001 to 0.1 mol/L, and more preferably 0.002 to 0.01 mol/L. The pH of the reduction solution after the sulfuric acid has been added is, for example, 2.4 or lower, preferably 2.3 or lower.

The reduction solution was incubated for a predetermined time, whereby the dye reagent is reduced by the blood in the reduction solution. The incubation temperature is, for example, 1° C. to 10° C., and the incubation time is, for example, 0 to 5 minutes.

Next, the peak wavelength of the reduction solution after being reduced is measured optically. The peak wavelength is in the range from 450 to 550 nm, for example.

The reducing power of the blood can be analyzed in the above-described manner. Also, using an optical signal obtained by the optical measurement of the peak wavelength, the reducing power can be determined by calculating the value of the reducing power on the basis of the correlation between the optical signal and the reducing power.

<Reducing Power Analysis Reagent>

As described above, the reducing power analysis reagent according to the present invention is a reagent for use in the analysis method of the present invention, containing: a dye reagent containing a ferric compound and a cyanide; and a pH adjuster, wherein the pH adjuster is a strongly acidic reagent. The analysis reagent of the present invention is characterized in that it contains the above-described pH adjuster, and other configurations and conditions are not particularly limited. The above descriptions regarding the analysis method of the present invention also apply to the analysis reagent of the present invention, for example. The analysis reagent of the present invention also can be referred to as, for example, an analysis kit.

In the analysis reagent of the present invention, the dye reagent and the pH adjuster may be contained separately in different containers, or may be contained in the same container in a mixed or unmixed state, for example. The ferric compound and the cyanide as the components of the dye reagent may be contained separately in different containers, or may be contained in the same container in a mixed or unmixed state, for example. When the ferric compound and the cyanide are contained in the same container, the dye reagent preferably is a solution containing the ferric compound and the cyanide.

The analysis reagent of the present invention further may contain an additional reagent(s), in addition to the dye reagent containing the ferric compound and the cyanide and the pH adjuster. The additional reagent is not particularly limited, and examples thereof include surfactants, organic solvents, and salts. The additional reagent may be contained in a container different from the container of the dye reagent or the pH adjuster, may be contained in the same container with either the dye reagent or the pH adjuster in a mixed or unmixed state, or may be contained in the same container with both the dye reagent and the pH adjuster, for example. When the analysis reagent of the present invention is an analysis kit, the analysis kit of the present invention further may include instructions for use, for example.

EXAMPLES

Next, examples of the present invention will be described. It is to be noted, however, that the present invention is by no means limited by the following examples.

Example 1

The present example examined whether the peak wavelength shift occurs in a sample containing albumin or methionine, and also examined whether the peak wavelength shift can be prevented by setting the pH of a reduction solution (reaction solution) in the reduction step to 2.4 or lower.

(1) Examination on Peak Wavelength Shift

An albumin sample was prepared by adding human serum albumin to physiological saline at a concentration of 0.5 g/L. Also, a methionine sample was prepared by adding methionine to physiological saline at a concentration of 0.5 g/L.

Next, a mixed dye reagent 1 was prepared by adding, to distilled water, potassium thiocyanate at a concentration of 60 mmol/L and iron(III) chloride at a concentration of 0.25 mmol/L. The mixed dye reagent 1 and the albumin or methionine sample were mixed at a ratio (volume ratio) of 49:1. After the mixing, the resultant mixture was incubated at 25° C. for 3 minutes.

Then, the absorbance of the reduction solution after the incubation was measured in a wavelength range from 400 to 800 nm using an absorptiometer (trade name: V-550, JASCO Corporation). As a control, the absorbance of the mixed dye reagent 1 was measured in a wavelength range from 400 to 800 nm. The pH of the reduction solution in the reduction step was: 2.7 in the case of the reduction solution containing the albumin sample; and 2.7 in the case of the reduction solution containing the methionine sample.

The results thereof are shown in FIG. 1. FIG. 1 is a graph showing the results of measuring the absorbance of each reduction solution. In FIG. 1, the horizontal axis indicates the wavelength, and the vertical axis indicates the absorbance. As can be seen from FIG. 1, while the peak wavelength was observed in the vicinity of 480 nm in the control, the peak wavelength was observed in a wavelength region of 400 nm or shorter in the albumin sample and the methionine sample. These results demonstrate that, in each of the albumin sample and the methionine sample, the peak wavelength shifted to a shorter wavelength, as compared with the control.

(2) Examination on Prevention of Peak Wavelength Shift by Strongly Acidic Conditions A mixed dye reagent 2 was prepared by adding, to distilled water, potassium thiocyanate at a concentration of 60 mmol/L and iron(III) chloride at a concentration of 0.25 mmol/L. Subsequently, as the pH adjuster, sulfuric acid, which is the strongly acidic reagent, further was added thereto at a concentration of 30 mmol/L. Then, except that the mixed dye reagent 2 was used instead of the mixed dye reagent 1 and that the mixed dye reagent 2 and the albumin sample were mixed at a ratio (volume ratio) of 80:1, the absorbance was measured in the same manner as in the above item (1) in a wavelength range from 370 to 650 nm (Example). The pH of the reduction solution was 2.1. Also, the absorbance was measured in a wavelength range from 370 to 650 nm in the same manner as in the above in Controls 1 to 3, except that the physiological saline and the mixed dye reagent 1 were used in Control 1, the albumin sample and the mixed dye reagent 1 were used in Control 2, and the physiological saline and the mixed dye reagent 2 were used in Control 3.

Figure 2:
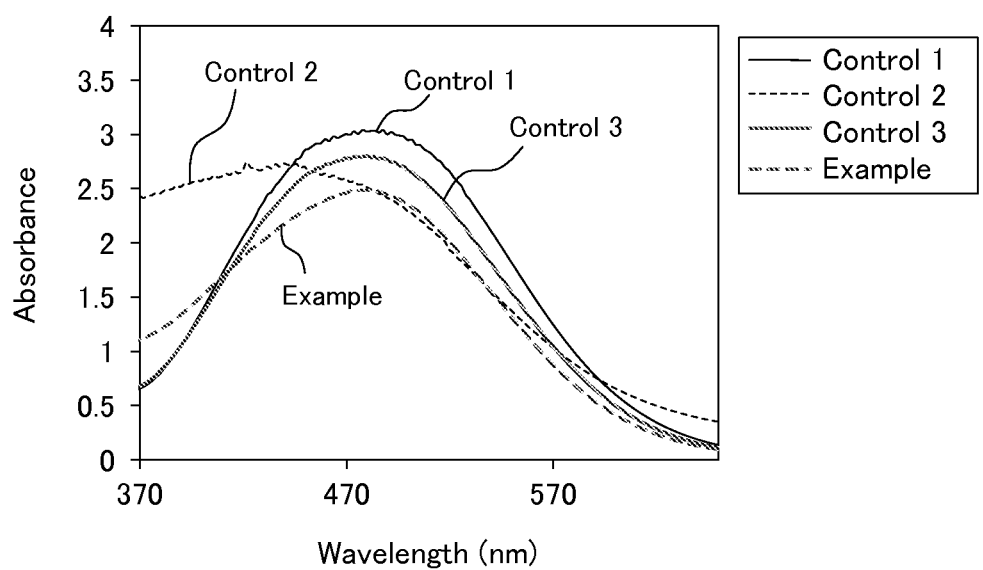
FIG. 2 is a graph showing the results of absorbance measurements in Example 1.

The results are shown in FIG. 2. FIG. 2 is a graph showing the results of measuring the absorbance of each reduction solution. In FIG. 2, the horizontal axis indicates the wavelength, and the vertical axis indicates the absorbance. As can be seen from FIG. 2, in Controls 1 and 3 where the reduction solutions did not contain albumin, the peak wavelengths were observed in the vicinity of 480 nm. In Control 2 where the reduction solution contained albumin, the peak wavelength was observed in the vicinity of 440 nm, so that the peak wavelength shifted to a shorter wavelength, as compared with Controls 1 and 3 where the reduction solutions did not contain either albumin or methionine. In contrast, in the example where the pH of the reduction solution was 2.4 or lower, the peak wavelength was observed in the vicinity of 480 nm. These results demonstrate that, by setting the pH of the reduction solution in the reduction step to 2.4 or lower, the peak wavelength shift can be prevented.

Example 2

In the present example, different pH adjusters were used to examine whether the peak wavelength shift in a sample containing albumin can be prevented by setting the pH of a reduction solution in the reduction step to 2.4 or lower.

To physiological saline, potassium thiocyanate was added at a concentration of 60 mmol/L and iron(III) chloride was added at a concentration of 0.25 mmol/L. Mixed dye reagents 3 to 6 were prepared by further adding sulfuric acid, which is the strongly acidic reagent, as the pH adjuster so that the pHs of reduction solutions to be obtained after being mixed with the sample became 2.1, 2.3, 2.5, and 2.8, respectively. Also, mixed dye reagents 7 to 10 were prepared by adding propionic acid instead of the sulfuric acid so that the pHs of reduction solutions to be obtained after being mixed with the sample became 2.0, 2.3, 2.6, and 2.7, respectively. Further, mixed dye reagents 11 to 14 were prepared by adding p-toluenesulfonic acid instead of the sulfuric acid so that the pH's of reduction solutions to be obtained after being mixed with the sample became 2.0, 2.4, 2.6, and 2.8, respectively.

Next, except that the mixed dye reagents 3 to 14 were used instead of the mixed dye reagent 2, the absorbance was measured in a wavelength range from 300 to 650 nm in the same manner as in Example 1.

The results thereof are shown in FIGS. 3A-3C. FIGS. 3A-3C are graphs, with each showing the results of measuring the absorbance of each reduction solution. FIG. 3A shows the results obtained when the sulfuric acid was used; FIG. 3B shows the results obtained when the propionic acid was used, and FIG. 3C shows the results obtained when the p-toluenesulfonic acid was used. In each of FIGS. 3A to 3C, the horizontal axis indicates the wavelength, and the vertical axis indicates the absorbance. As can be seen from FIG. 3A, when the sulfuric acid was used as the pH adjuster, the peak wavelengths were observed in the vicinity of 470 nm in the case of the mixed dye reagents 5 and 6 with which the reduction solutions having a pH higher than 2.4 were provided, whereas the peak wavelengths were observed in the vicinity of 480 nm in the case of the mixed dye reagents 3 and 4 the pH of the reduction solution with which the reduction solutions having a pH of 2.4 or lower were provided. Furthermore, as can be seen from FIG. 3B, when the propionic acid was used as the pH adjuster, the peak wavelengths were observed in the vicinity of 460 to 470 nm in the case of the mixed dye reagents 9 and 10 with which the reduction solutions having a pH higher than 2.4 were provided, whereas the peak wavelengths were observed in the vicinity of 480 nm in the case of the mixed dye reagents 7 and 8 with which the reduction solutions having a pH of 2.4 or lower were provided. Still further, as can be seen from FIG. 3C, when the p-toluenesulfonic acid was used as the pH adjuster, the peak wavelengths were observed in the vicinity of 460 to 470 nm in the case of the mixed dye reagents 13 and 14 with which the reduction solutions having a pH higher than 2.4 were provided, whereas the peak wavelengths were observed in the vicinity of 480 nm in the case of the mixed dye reagents 11 and 12 with which the reduction solutions having a pH of 2.4 or lower were provided. These results demonstrate that, when any of the pH adjusters is used, the peak wavelength shift is prevented by setting the pH of the reduction solution in the reduction step to 2.4 or lower.

Figure 4:
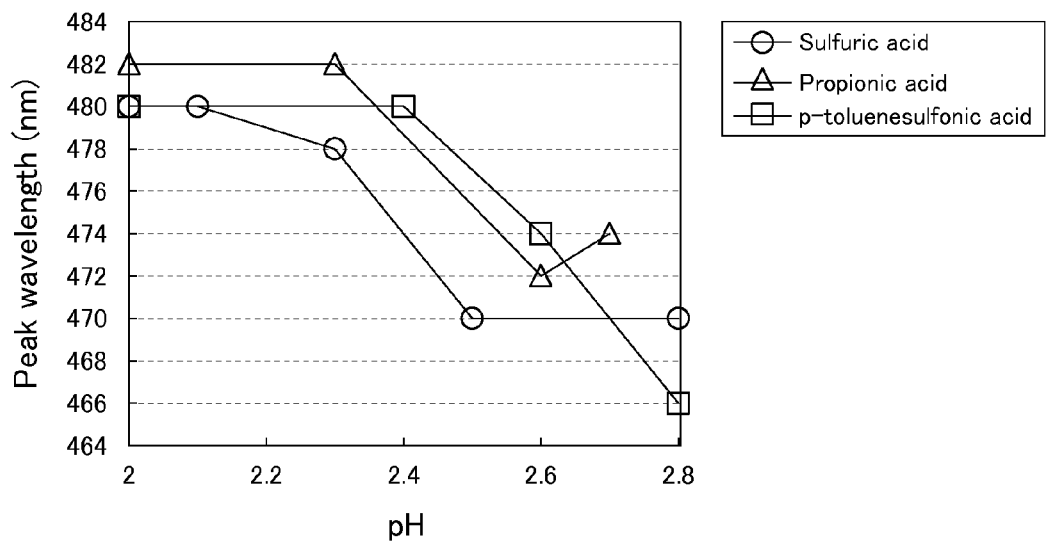
FIG. 4 is a graph showing peak wavelengths at different pH values in Example 2.

The graph of FIG. 4 collectively shows the peak wavelengths in the wavelength range from 400 to 600 nm in the case where the mixed dye reagents 3 to 14 were used.

FIG. 4 is a graph showing the peak wavelengths at different pHs. In FIG. 4, the horizontal axis indicates the pH, and the vertical axis indicates the peak wavelength. As can be seen from FIG. 4, when any of the pH adjusters, namely, the sulfuric acid (open circle: ○), the propionic acid (open triangle: △), and the p-toluenesulfonic acid (open square: □), was used, the peak wavelength shift was prevented more effectively as the pH of the reduction solution in the reduction step became lower. Moreover, when the pH of the reduction solution in the reduction step was 2.4 or lower, the peak wavelength was substantially constant. These results demonstrate that, by setting the pH of the reduction solution in the reduction step to 2.4 or lower, it is possible to prevent the peak wavelength from shifting in a sample containing albumin, even when different pH adjusters are used.

Example 3

The present example examined whether the reducing power analysis method according to the present invention can analyze the reducing power of a biological sample.

The absorbance was measured at 476 nm in the same manner as in Example 1(2), except that human serum samples (n=4) were used instead of a sample containing albumin. Also, a reference standard with a reducing power of 10,000 μmol/L was subjected to 2-fold serial dilution with physiological saline to provide a dilution series up to 8-fold. These diluted solutions were used as standard samples. Then, except for the fact that these standard samples were used instead of the human serum sample, the absorbance was measured at 476 nm in the same manner.

Next, a standard curve was prepared on the basis of the reducing powers and the absorbances of the standard samples. Then, the reducing power of the human serum sample was calculated with reference to the standard curve.

Figure 5:
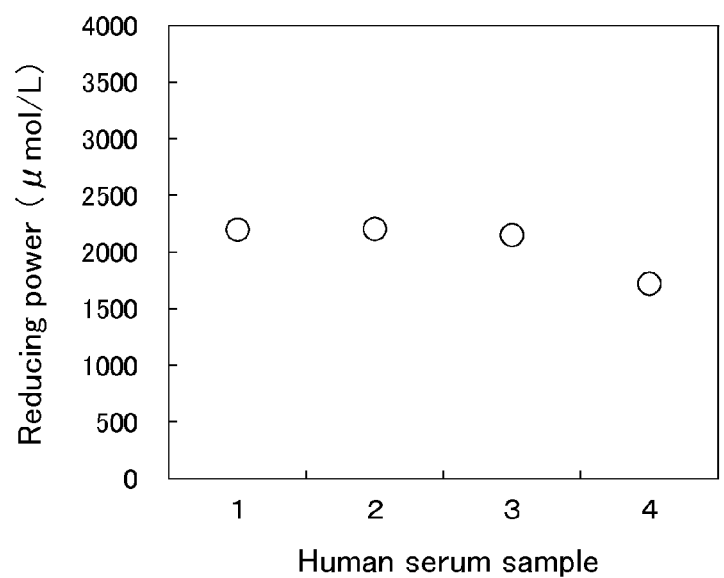
FIG. 5 is a graph showing the results of reducing power measurements in Example 3.

The results thereof are shown in FIG. 5. FIG. 5 is a graph showing the results of measuring the reducing power of each human serum sample. In FIG. 5, the horizontal axis indicates the kind of the human serum sample, and the vertical axis indicates the reducing power. As can be seen from FIG. 5, the reducing powers of all the human serum samples could be measured. These results demonstrate that, according to the analysis method of the present invention, the reducing power of a biological sample can be analyzed with higher reliability.

While the present invention has been described above with reference to embodiments and examples, the present invention is by no means limited thereto. Various changes and modifications that may become apparent to those skilled in the art may be made in the configuration and specifics of the present invention without departing from the scope of the present invention.

This application claims priority from Japanese Patent Application No. 2015-054883 filed on Mar. 18, 2015 and from Japanese Patent Application No. 2014-063735 filed on Mar. 26, 2014. The entire disclosure of each of these Japanese patent applications is incorporated herein by reference.

INDUSTRIAL APPLICABILITY

According to the present invention, it is possible to prevent a shift in the peak wavelength in an absorption spectrum when the reducing power of a sample is employed. Therefore, it is possible to minimize errors resulting from when the reducing power of a sample is analyzed on the basis of the peak wavelength of an optical signal, so that the reducing power of a sample can be analyzed with higher reliability. Accordingly, the present invention is very useful in clinical tests and the like of various biological samples derived from living organisms and the like, for example.

What is claimed is:

1. A method for analyzing reducing power of a sample, comprising:
reducing a solution of an iron-cyanide complex over a pH range beginning at 2.4 and lower in the presence of a sample comprising at least one of albumin and methionine, where the pH range is achieved by adding p-toluenesulfonic acid to the solution;

optically measuring a peak wavelength in a range of from 360 to 630 nm of the reduced iron-cyanide complex obtained in the reducing step;

wherein the iron in the iron-cyanide complex is at least one of iron(III) chloride and iron(III) sulfate, and wherein the cyanide in the iron-cyanide complex is at least one of a ferricyanide and a thiocyanate selected from the group consisting of potassium thiocyanate, sodium thiocyanate and ammonium thiocyanate.

2. The method according to claim 1, wherein the sample is at least one selected from the group consisting of blood, saliva, urine, tear, and sweat.

3. The method according to claim 2, wherein the sample is blood.

4. The method according to claim 3, wherein the blood is whole blood.

5. The method according to claim 1, wherein the molar ratio between the iron and the cyanide in the iron-cyanide complex solution is 1:72 to 1:357.

6. The method according to claim 1, wherein the concentration of the cyanide contained in the iron-cyanide complex solution is 0.018 to 0.09 mol/L.

7. The method according to claim 1, wherein the concentration of the iron contained in the iron-cyanide complex solution is 0.018 to 0.09 mol/L.

8. The method according to claim 1, wherein the reducing step occurs at a temperature of 1 to 40° C.

9. The method according to claim 1, wherein the peak wavelength is in a range of 400 to 550 nm.

10. The method according to claim 1, wherein the thiocyanate is potassium thiocyanate.

11. The method according to claim 1, wherein the sample comprises albumin.

12. The method according to claim 1, wherein the sample comprises methionine.

* * * * *